United States Patent [19]

Van Wingerden

[11] Patent Number: Plant 6,851

[45] Date of Patent: Jun. 13, 1989

[54] CHRYSANTHEMUM NAMED CALIFORNIA MONEYMAKER

[75] Inventor: Rene Van Wingerden, Carpinteria, Calif.

[73] Assignee: California Plant Company, Carpinteria, Calif.

[21] Appl. No.: 131,851

[22] Filed: Dec. 11, 1987

[51] Int. Cl.[4] ..... A01H 5/00

[52] U.S. Cl. ..... Plt./74

[58] Field of Search ..... Plt./74

*Primary Examiner*—Robert E. Bagwill

[57] ABSTRACT

A new spray type Chrysanthemum particularly distinguished by the relatively narrow ray petals of its fully opened bloom of medium size, giving the flower a rather open appearance which provides a very attractive flower, the flowers being borne singly on individual stems of about 6 to 12 inches in length in a spray formation on the flowering stem of a bush having a height of from three to four feet, the plant itself being of a vigorous, upright growth habit with good strength.

1 Drawing Sheet

BACKGROUND OF THE INVENTION

This new Chrysanthemum variety was discovered by me as a sport of the variety 'Moneymaker' (patent applied for) being grown in my nursery at Carpinteria, Calif. The new flower caught my attention because of its somewhat darker color than that of the parent plant and because of its more open blossoms having a somewhat brighter appearance. I propagated this sport by means of cuttings with favorable results and further propagation through several successive generations has demonstrated that the novel characteristics of the new plant hold true from generation to generation and appear to be firmly fixed. Propagation of this new plant for eventual commerical marketing is being done by stem cuttings at the Westland Floral Nursery in Carpinteria and the plants of this variety appear to have a character of worthwhile commercial value.

DESCRIPTION OF THE DRAWINGS

This new Chrysanthemum variety is illustrated by the accompanying drawing which, in the upper view, shows a mature blossom depicting its form and coloration; and in the lower view shows the new variety in side-by-side relation with the parent to illustrate the characteristic differences.

DESCRIPTION OF THE NEW VARIETY

The following is a detailed description of my new Chrysanthemum based upon observation in the late summer of 1987 of plants being grown at Westland Floral Nursery in Carpinteria, Calif. The color designations are according to The R.H.S. Colour Chart published by The Royal Horticultural Society of London, England.

THE PLANT

Origin: Sport.

Parentage: A Chrysanthemum variety named 'Moneymaker' (patent applied for).

Classification:

*Botanic.*—*Chrysanthemum morifolium;* Ramat.

*Commercial.*—Chrysanthemum.

Form: Upright herbaceous perennial bush.

Height: About 3 to 4 feet.

Main stem length: Approximately 3½ feet.

Growth habit: Vigorous, upright, with good strength.

Branching character: Prolific, if pinched.

Foliage:

*Quantity.*—Abundant.

*Number of leaves.*—Typically about 16.

*Leaf size.*—Medium. Length — About 6 to 12 inches.

THE BUD

Shape: Oval.

Size:

*Diameter.*—About ⅝ inch.

*Depth.*—About ⅜ to ⅝ inch.

Rate of opening: Fairly fast.

Color of florets: When sepals first divide, Rose Purple 75-B.

*When petals begin to unfurl.*—Outside, 186-B; inside 75-A.

Sepals: Spear shaped and about 18 in number. The sepals are hooded over the bud and attached at the base but are separated at the distal ends.

*Character.*—The sepals curl back when the flowers open.

*Color.*—Inside and outside, 146-A.

Calyx:

*Shape.*—Funnel shaped.

*Size.*—Broad.

*Splitting.*—The calyx does split.

*Aspect.*—Smooth.

Flower stem: About 6 to 12 inches.

THE FLOWER

Blooming habit: Recurrent with controlled photoperiod, blooming naturally in the fall.

Size: Medium.

*Diameter.*—About 2 to 2¾ inches when two-thirds open.

*Depth.*—About ⅜ to ⅝ inch.

Borne: Singly, as part of a spray arrangement.

Form:

*When bloom first opens.*—Cup-shaped with high center.

*When bloom matures.*—Flat.

Petalage:

*Number of florets.*—Ray — About 27 to 31. Disc — About 150 to 170.

*Arrangement.*—Whorled on receptacle.

*Form.*—Oblong with entire margins and mucronate tip.

*Texture.*—Soft.

*Aspect.*—Satiny.

*Color.*—Outer Floret: Body — 75-C. Base — 151-D. Reverse side — 76-D. Inside Floret: Body — 78-C. Base — 151-C. Immature Distal Tips — 161-D. Reverse Side — 76-C.

Flower Stem:

*Length.*—About 6 to 12 inches.

*Color.*—146-B.

*Character.*—Upright and rigid.

Discoloration after full bloom: The color becomes slightly lighter.

Effect of Weather: The color fades slightly in hot weather.

Persistence: The flowers hang on and dry.

Fragrance: Typical for Chrysanthemum.

Lasting quality: Good, both on the plant and as a cut flower.

THE REPRODUCTIVE ORGANS

Stamens and anthers: None.

Pistils:

*Number.*—About 150 to 180.

*Styles.*—Length: About 0.5 cm. Color: 3-B.

*Stigmas.*—Color: 17-B.

Character of ovaries: Small, slender and white in color.

This new Chrysanthemum variety most nearly resembles 'Moneymaker' (patent applied for) but the new plant has slightly fewer ray florets and the flower color is much darker than that of 'Moneymaker'. The difference between the sport and its parent is shown by the following flower comparison table which is based on flower comparisons made at Westland Floral Nursery in September of 1987 at Carpinteria, Calif.

| | | California Moneymaker | Moneymaker |
|---|---|---|---|
| Petalage | No. of Ray Florets | 27–31 | 30–33 |
| | No. of Disc Florets | 150–170 | 160–180 |
| Ray Floret | Body Color | 75-C | 75-D |
| | Reverse Color | 76-D | 56-D |
| | Base Color | 151-D | 154-A |
| Disc Floret | Body Color | 78-C | 75-D |
| | Reverse Color | 76-C | 56-D |
| | Base Color | 151-C | 151-B |
| | Distal Tips | 161-D | 179-D |

The flower colors may vary with season and environmental conditions; however, 'California Moneymaker' is always darker than 'Moneymaker'.

I claim:

1. The new and distinct variety of Chrysanthemum plant and the parts thereof, substantially as herein shown and described, characterized by its profuse recurrent production of medium sized flowers with controlled photoperiod, being borne singly on straight stems growing from a main stem in a spray manner, the plant branching prolifically, if pinched, with vigorous, upright stems of good strength.

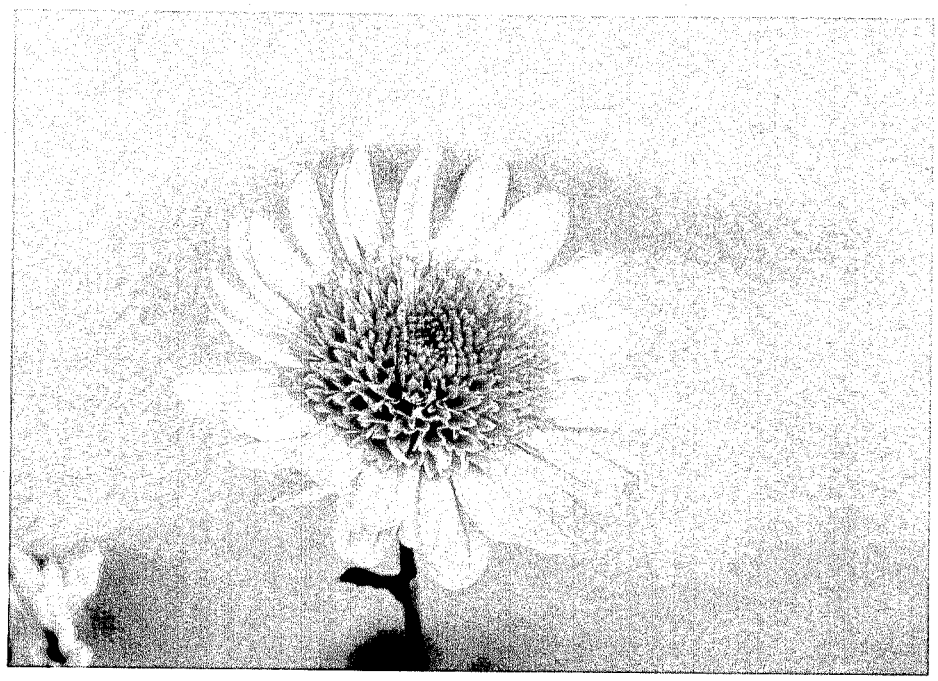
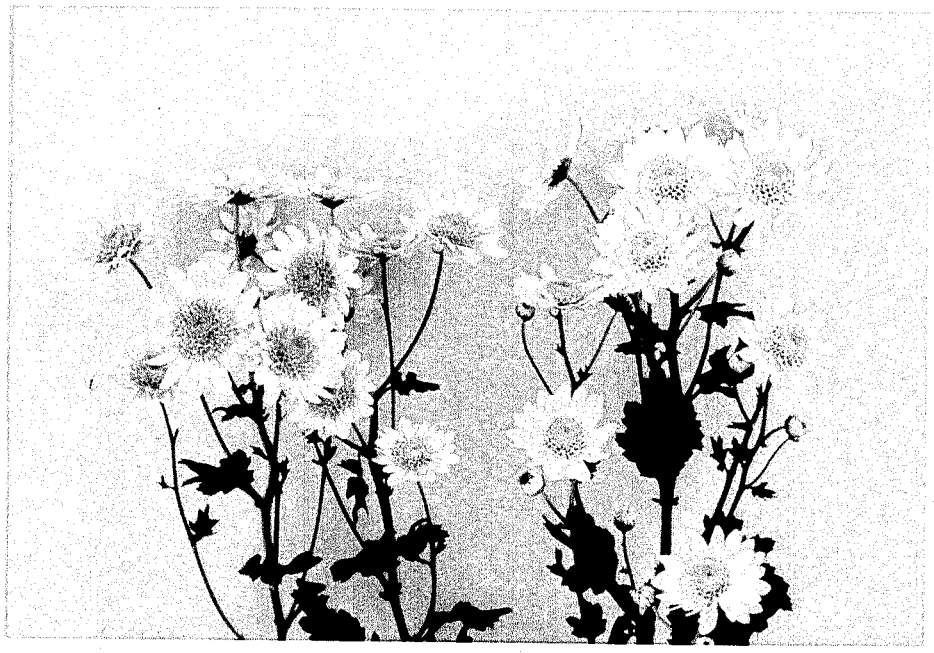

* * * * *